(12) United States Patent
Brandenburg et al.

(10) Patent No.: US 7,148,347 B2
(45) Date of Patent: Dec. 12, 2006

(54) PROCESS FOR PREPARING MACROCYCLIC COMPOUNDS

(75) Inventors: Joerg Brandenburg, Wiesbaden (DE); Kai Donsbach, Glen Allen, VA (US); Hans-Dieter Ecker, Gau-Algesheim (DE); Rogelio Perez Frutos, Sandy Hook, CT (US); Fabrice Gallou, Danbury, CT (US); Dieter Gutheil, Bad Kreuznach (DE); Nizar Haddad, Danbury, CT (US); Robert Hagenkoetter, Idstein (DE); Dirk Kemmer, Guldental (DE); Jutta Kroeber, Bingen-Dietersheim (DE); Thomas Nicola, Ingelheim (DE); Juergen Schnaubelt, Biberach (DE); Michael Schul, Plaidt (DE); Robert Donald Simpson, Wilmington, DE (US); Xudong Wei, Ridgefield, CT (US); Eric Winter, Gau-Algesheim (DE); Yibo Xu, New Milford, CT (US); Nathan K. Yee, Danbury, CT (US)

(73) Assignee: Boehringer Ingelheim International GmbH, Ingelheim (DE)

( * ) Notice: Subject to any disclaimer, the term of this patent is extended or adjusted under 35 U.S.C. 154(b) by 161 days.

(21) Appl. No.: 10/818,657

(22) Filed: Apr. 6, 2004

(65) Prior Publication Data

US 2005/0049187 A1    Mar. 3, 2005

Related U.S. Application Data

(60) Provisional application No. 60/461,662, filed on Apr. 10, 2003.

(51) Int. Cl.
*C07D 207/09* (2006.01)
*C07D 245/04* (2006.01)
*C07D 267/02* (2006.01)

(52) U.S. Cl. .................. 540/460; 540/546; 548/537
(58) Field of Classification Search ............... None
See application file for complete search history.

(56) References Cited

U.S. PATENT DOCUMENTS

| | | | |
|---|---|---|---|
| 6,323,180 B1 | 11/2001 | Llinas-Brunet et al. | 514/18 |
| 6,534,523 B1 | 3/2003 | Llinas-Brunet | 514/312 |
| 6,608,027 B1 | 8/2003 | Tsantrizos et al. | 514/9 |
| 2004/0248779 A1 | 12/2004 | Dersch et al. | 514/9 |
| 2005/0080005 A1 | 4/2005 | Llinas-Brunet et al. | |

FOREIGN PATENT DOCUMENTS

| | | |
|---|---|---|
| WO | WO 00/09543 A2 | 2/2000 |
| WO | WO 00/09558 A1 | 2/2000 |
| WO | WO 00/59929 A1 | 10/2000 |

OTHER PUBLICATIONS

Llinas-Brunet, M. et al; "Macrocyclic Peptides Active Against The Hepatitis C Virus"; U.S. Appl. No. 10/686,755, filed Oct. 16, 2003.

*Primary Examiner*—Jeffrey Edwin Russel
(74) *Attorney, Agent, or Firm*—Michael P. Morris; Mary Ellen M. Devlin; Philip I. Datlow

(57) ABSTRACT

Disclosed is a process for preparing a macrocyclic compound of the formula (I):

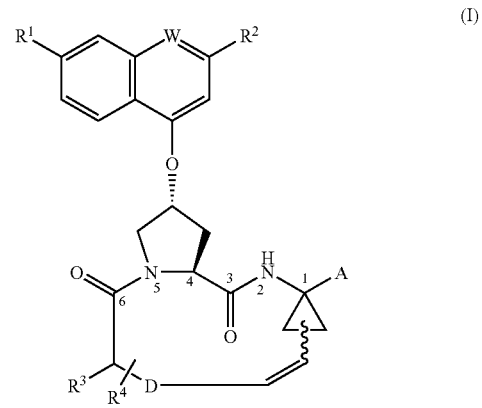

which is carried out using an intermediate of the formula (II):

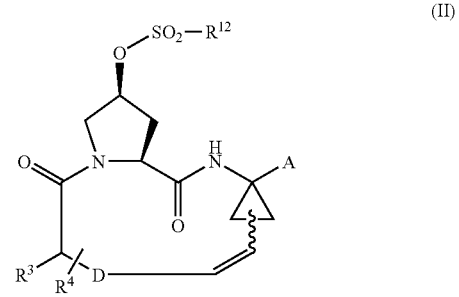

wherein W, $R^1$ through $R^4$, D, A and $R^{12}$ are as defined herein. The compounds of formula (I) are potent active agents for the treatment of hepatitis C virus (HCV) infection.

22 Claims, No Drawings

US 7,148,347 B2

PROCESS FOR PREPARING MACROCYCLIC COMPOUNDS

This application claims benefit from U.S. Provisional Application No. 60/461,662, filed Apr. 10, 2003, which application is herein incorporated by reference in its entirety.

BACKGROUND OF THE INVENTION

1. Technical Field

The invention relates to an improved process for the preparation of macrocyclic compounds useful as agents for the treatment of hepatitis C viral (HCV) infections.

2. Background Information

The macrocyclic compounds of the following formula (I) are known from the International Patent Application WO 00/59929, U.S. application Ser. No. 09/760,946, filed Jan. 16, 2001, and U.S. Provisional Application No. 60/442,768, filed Jan. 27, 2003, all of which are herein incorporated by reference:

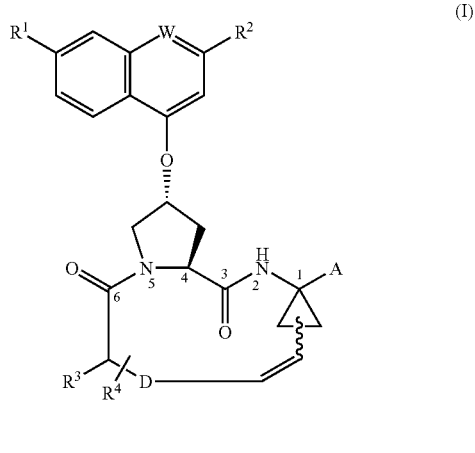

wherein W is CH or N,
$R^1$ is H, halo, $C_{1-6}$ alkyl, $C_{3-6}$ cycloalkyl, $C_{1-6}$ haloalkyl, $C_{1-6}$ alkoxy, $C_{3-6}$ cycloalkoxy, hydroxy, or $N(R^5)_2$,
wherein each $R^5$ is independently H, $C_{1-6}$ alkyl or $C_{3-6}$ cycloalkyl;
$R^2$ is H, halo, $C_{1-6}$ alkyl, $C_{3-6}$ cycloalkyl, $C_{1-6}$ haloalkyl, $C_{1-6}$ thioalkyl, $C_{1-6}$ alkoxy, $C_{3-6}$ cycloalkoxy, $C_{2-7}$ alkoxy-$C_{1-6}$ alkyl, $C_6$ or $C_{10}$ aryl or Het, wherein Het is a five-, six-, or seven-membered saturated or unsaturated heterocycle containing from one to four heteroatoms selected from nitrogen, oxygen and sulfur;
said cycloalkyl, aryl or Het being substituted with $R^6$,
wherein $R^6$ is H, halo, $C_{1-6}$ alkyl, $C_{3-6}$ cycloalkyl, $C_{1-6}$ alkoxy, $C_{3-6}$ cycloalkoxy, $NO_2$, $N(R^7)_2$, $NH—C(O)—R^7$; or $NH—C(O)—NH—R^7$, wherein each $R^7$ is independently: H, $C_{1-6}$ alkyl or $C_{3-6}$ cycloalkyl;
or $R^6$ is $NH—C(O)—OR^8$ wherein $R^8$ is $C_{1-6}$ alkyl or $C_{3-6}$ cycloalkyl;
$R^3$ is hydroxy, $NH_2$, or a group of formula $—NH—R^9$, wherein $R^9$ is $C_6$ or $C_{10}$ aryl, heteroaryl, $—C(O)—R^{10}$, $—C(O)—NHR^{10}$ or $—C(O)—OR^{10}$,
wherein $R^{10}$ is $C_{1-6}$ alkyl or $C_{3-6}$ cycloalkyl;
D is a 3 to 7-atom saturated alkylene chain;
$R^4$ is H, or from one to three substituents at any carbon atom of said chain D, said substituent independently selected from the group consisting of: $C_{1-6}$ alkyl, $C_{1-6}$ haloalkyl, $C_{1-6}$ alkoxy, hydroxy, halo, amino, oxo, thio, or $C_{1-6}$ thioalkyl; and
A is an amide of formula $—C(O)—NH—R^{11}$, wherein $R^{11}$ is selected from the group consisting of: $C_{1-8}$ alkyl, $C_{3-6}$ cycloalkyl, $C_6$ or $C_{10}$ aryl, $C_{7-16}$ aralkyl and $SO_2R^{11A}$ wherein $R^{11A}$ is $C_{1-8}$ alkyl, $C_{3-7}$ cycloalkyl or $C_{1-6}$ alkyl-$C_{3-7}$ cycloalkyl;
or A is a carboxylic acid or a pharmaceutically acceptable salt or ester thereof;

The compounds of formula (I) are disclosed as being active agents for the treatment of hepatitis C virus (HCV) infections. The methods disclosed for the preparation of these compounds include many synthetic steps, which involve protection and deprotection of certain reactive groups and leads to an insufficient overall yield. Moreover, the disclosed methods are difficult to implement on a technical scale. The problem underlying the present invention is to provide a process which allows for the manufacture of these compounds on a technical scale with sufficient overall yield.

BRIEF SUMMARY OF THE INVENTION

It has been found surprisingly that the compounds of formula (I) described above can be prepared on a technical scale if the synthesis is carried out using an intermediate compound of formula (II):

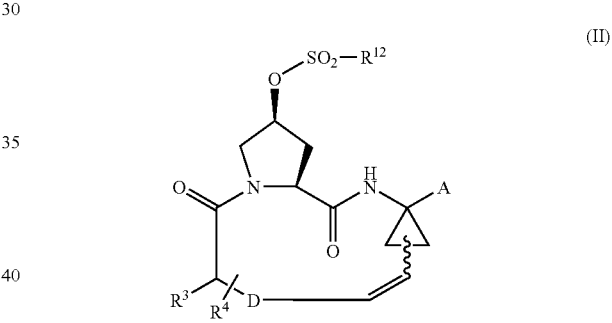

wherein $R^{12}$ is selected from a variety of different groups as described more fully herein. The present invention is therefore directed to a multi-step synthetic process for preparing compounds of formula (I) using compounds of formula (II) as intermediates; particular individual steps of this multi-step process; and particular individual intermediates used in this multi-step process.

DETAILED DESCRIPTION OF THE INVENTION

Definition of Terms and Conventions Used

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$ alkyl means an alkyl group or radical having 1 to 6 carbon atoms. In general, for groups comprising two or more subgroups, the last named group is the radical attachment point, for example, "thioalkyl" means a monovalent radical of the formula HS-Alk-. Unless otherwise specified below, conventional definitions of terms control and conventional stable atom valences are presumed and achieved in all formulas and groups.

The term "$C_{1-6}$ alkyl" as used herein, either alone or in combination with another substituent, means acyclic, straight or branched chain alkyl substituents containing from 1 to six carbon atoms and includes, for example, methyl, ethyl, propyl, butyl, hexyl, 1-methylethyl, 1-methylpropyl, 2-methylpropyl, and 1,1-dimethylethyl.

The term "$C_{3-6}$ cycloalkyl" as used herein, either alone or in combination with another substituent, means a cycloalkyl substituent containing from three to six carbon atoms and includes cyclopropyl, cyclobutyl, cyclopentyl, and cyclohexyl.

The term "saturated alkylene chain" as used herein means a divalent alkyl substituent derived by the removal of one hydrogen atom from each end of a saturated straight or branched chain aliphatic hydrocarbon and includes, for example,

—CH$_2$CH$_2$C(CH$_3$)$_2$CH$_2$CH$_2$—.

The term "$C_{1-6}$ alkoxy" as used herein, either alone or in combination with another substituent, means the substituent $C_{1-6}$ alkyl-O— wherein alkyl is as defined above containing up to six carbon atoms. Alkoxy includes methoxy, ethoxy, propoxy, 1-methylethoxy, butoxy and 1,1-dimethylethoxy. The latter substituent is known commonly as tert-butoxy.

The term "$C_{3-6}$ cycloalkoxy" as used herein, either alone or in combination with another substituent, means the substituent $C_{3-6}$ cycloalkyl-O— containing from 3 to 6 carbon atoms.

The term "$C_{2-7}$ alkoxy-$C_{1-6}$alkyl" as used herein, means the substituent $C_{2-7}$ alkyl-O—$C_{1-6}$ alkyl wherein alkyl is as defined above containing up to six carbon atoms.

The term "halo" as used herein means a halogen substituent selected from bromo, chloro, fluoro or iodo.

The term "haloalkyl" as used herein means as used herein, either alone or in combination with another substituent, means acyclic, straight or branched chain alkyl substituents having one or more hydrogens substituted for a halogen selected from bromo, chloro, fluoro or iodo.

The term "thioalkyl" as used herein means as used herein, either alone or in combination with another substituent, means acyclic, straight or branched chain alkyl substituents containing a thiol (HS) group as a substituent. An example of a thioalkyl group is a thiopropyl, e.g., HS—CH$_2$CH$_2$CH$_2$— is one example of a thiopropyl group.

The term "$C_6$ or $C_{10}$ aryl" as used herein, either alone or in combination with another substituent, means either an aromatic monocyclic system containing 6 carbon atoms or an aromatic bicyclic system containing 10 carbon atoms. For example, aryl includes a phenyl or a naphthyl ring system.

The term "$C_{7-16}$ aralkyl" as used herein, either alone or in combination with another substituent, means an aryl as defined above linked through an alkyl group, wherein alkyl is as defined above containing from 1 to 6 carbon atoms. Aralkyl includes for example benzyl, and butylphenyl.

The term "Het" as used herein, either alone or in combination with another substituent, means a monovalent substituent derived by removal of a hydrogen from a five-, six-, or seven-membered saturated or unsaturated (including aromatic) heterocycle containing carbon atoms and from one to four ring heteroatoms selected from nitrogen, oxygen and sulfur. Examples of suitable heterocycles include: tetrahydrofuran, thiophene, diazepine, isoxazole, piperidine, dioxane, morpholine, pyrimidine or

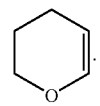

The term "Het" also includes a heterocycle as defined above fused to one or more other cycle be it a heterocycle or any other cycle. One such examples includes thiazolo[4,5-b]-pyridine. Although generally covered under the term "Het", the term "heteroaryl" as used herein precisely defines an unsaturated heterocycle for which the double bonds form an aromatic system. Suitable example of heteroaromatic system include: quinoline, indole, pyridine,

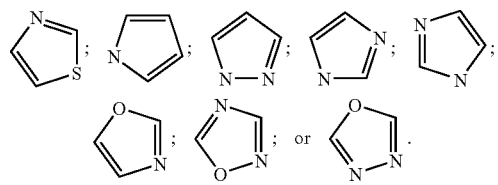

The term "oxo" means the double-bonded group (=O) attached as a substituent.

The term "thio" means the double-bonded group (=S) attached as a substituent.

In general, all tautomeric forms and isomeric forms and mixtures, whether individual geometric isomers or optical isomers or racemic or non-racemic mixtures of isomers, of a chemical structure or compound is intended, unless the specific stereochemistry or isomeric form is specifically indicated in the compound name or structure.

The term "pharmaceutically acceptable ester" as used herein, either alone or in combination with another substituent, means esters of the compound of formula I in which any of the carboxyl functions of the molecule, but preferably the carboxy terminus, is replaced by an alkoxycarbonyl function:

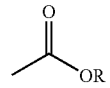

in which the R moiety of the ester is selected from alkyl (e.g. methyl, ethyl, n-propyl, t-butyl, n-butyl); alkoxyalkyl (e.g. methoxymethyl); alkoxyacyl (e.g. acetoxymethyl); aralkyl (e.g. benzyl); aryloxyalkyl (e.g. phenoxymethyl); aryl (e.g. phenyl), optionally substituted with halogen, $C_{1-4}$ alkyl or $C_{1-4}$ alkoxy. Other suitable prodrug esters are found in *Design of Prodrugs*, Bundgaard, H. Ed. Elsevier (1985) incorporated herewith by reference. Such pharmaceutically acceptable esters are usually hydrolyzed in vivo when injected in a mammal and transformed into the acid form of the compound of formula I. With regard to the esters described above, unless otherwise specified, any alkyl moiety present advantageously contains 1 to 16 carbon atoms, particularly 1 to 6 carbon atoms. Any aryl moiety present in such esters advantageously comprises a phenyl group. In particular the esters may be a $C_{1-16}$ alkyl ester, an unsubstituted benzyl ester or a benzyl ester substituted with at least one halogen, $C_{1-6}$ alkyl, $C_{1-6}$ alkoxy, nitro or trifluoromethyl.

The term "pharmaceutically acceptable salt" as used herein includes those derived from pharmaceutically acceptable bases. Examples of suitable bases include choline, ethanolamine and ethylenediamine. $Na^+$, $K^+$, and $Ca^{++}$ salts are also contemplated to be within the scope of the invention (also see *Pharmaceutical Salts*, Birge, S. M. et al., J. Pharm. Sci., (1977), 66, 1–19, incorporated herein by reference).

The following chemicals may be referred to by these abbreviations:

| Abbreviation | Chemical Name |
|---|---|
| Boc | Tert-butoxylcarbonyl |
| DABCO | 1,4-diazabicyclo[2.2.2]octane |
| DBU | 1,8-Diazabicyclo[5.4.0]undec-7-ene |
| DCC | 1,3-Dicyclohexylcarbodiimide |
| DCHA | Dicyclohexylamine |
| DIPEA | Diisopropylethylamine or Hünigs-Base |
| DMAP | Dimethylaminopyridine |
| DMF | N,N-Dimethylformamide |
| DMSO | Dimethylsulfoxide |
| DMTMM | 4-(4,6-Dimethoxy-1,3,5-triazin-2-yl)-4-methylmorpholinium Chloride |
| EDC | 1-(3-dimethylaminopropyl)-3-ethylcarbodiimide hydrocholide |
| HATU | O-(7-azabenzotriazol-1-yl)-N,N,',N'-tetramethyluronium hexafluorophosphate |
| HBTU | O-Benzotriazol-1-yl-N,N,',N'-tetramethyluronium hexafluorophosphate |
| HOAT | 1-Hydroxy-7-azabenzotriazole |
| HOBT | 1-Hydroxybenzotriazole |
| MCH | Methylcyclohexane |
| MIBK | 4-Metyl-2-pentanone |
| NMP | 1-Methyl-2-pyrrolidinone |
| SEH | Sodium 2-ethylhexanoate |
| TBTU | O-(Benzotriazol-1-yl)-N,N,N',N'-tetramethyluronium tetrafluoroborate |
| THF | Tetrahydofuran |
| THP | Trishydroxymethylphosphine |

EMBODIMENTS OF THE INVENTION

In the synthetic schemes below, unless specified otherwise, all the substituent groups in the chemical formulas shall have the same meanings as in the Formula (I). The reactants used in the synthetic schemes described below may be obtained either as described herein, or if not described herein, are themselves either commercially available or may be prepared from commercially available materials by methods known in the art. Certain starting materials, for example, may be obtained by methods described in the International Patent Applications WO 00/59929, WO 00/09543 and WO 00/09558 and U.S. Pat. No. 6,323,180 B1.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by High Pressure Liquid Chromatography (HPLC), if desired, and intermediates and products may be purified by chromatography on silica gel and/or by recrystallization.

I. General Multi-Step Synthetic Method

In one embodiment, the present invention is directed to a general multi-step synthetic method for preparing the compounds of formula (I). Specifically, this embodiment is directed to a process for preparing a compound of the following formula (I):

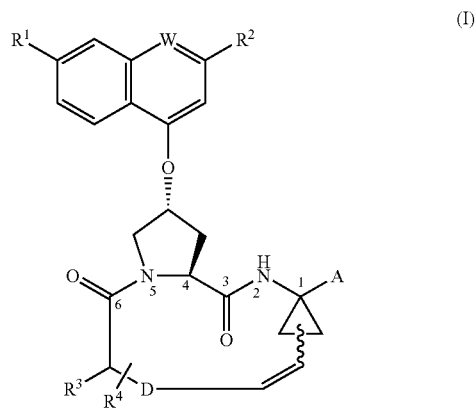

wherein W is CH or N, $R^1$ is H, halo, $C_{1-6}$ alkyl, $C_{3-6}$ cycloalkyl, $C_{1-6}$ haloalkyl, $C_{1-6}$ alkoxy, $C_{3-6}$ cycloalkoxy, hydroxy, or $N(R^5)_2$, wherein each $R^5$ is independently H, $C_{1-6}$ alkyl or $C_{3-6}$ cycloalkyl;

$R^2$ is H, halo, $C_{1-6}$ alkyl, $C_{3-6}$ cycloalkyl, $C_{1-6}$ haloalkyl, $C_{1-6}$ thioalkyl, $C_{1-6}$ alkoxy, $C_{3-6}$ cycloalkoxy, $C_{2-7}$ alkoxy-$C_{1-6}$alkyl, $C_6$ or $C_{10}$ aryl or Het, wherein Het is a five-, six-, or seven-membered saturated or unsaturated heterocycle containing from one to four heteroatoms selected from nitrogen, oxygen and sulfur;

said cycloalkyl, aryl or Het being substituted with $R^6$, wherein $R^6$ is H, halo, $C_{1-6}$ alkyl, $C_{3-6}$ cycloalkyl, $C_{1-6}$ alkoxy, $C_{3-6}$ cycloalkoxy, $NO_2$, $N(R^7)_2$, NH—C(O)—$R^7$; or NH—C(O)—NH—$R^7$, wherein each $R^7$ is independently: H, $C_{1-6}$ alkyl or $C_{3-6}$ cycloalkyl;

or $R^6$ is NH—C(O)—$OR^8$ wherein $R^8$ is $C_{1-6}$ alkyl or $C_{3-6}$ cycloalkyl;

$R^3$ is hydroxy, $NH_2$, or a group of formula —NH—$R^9$, wherein $R^9$ is $C_6$, or $C_{10}$ aryl, heteroaryl, —C(O)—$R^{10}$, —C(O)—$NHR^{10}$ or —C(O)—$OR^{10}$, wherein $R^{10}$ is $C_{1-6}$ alkyl or $C_{3-6}$ cycloalkyl;

D is a 3 to 7-atom saturated alkylene chain;

$R^4$ is H, or from one to three substituents at any carbon atom of said chain D, said substituent independently selected from the group consisting of: $C_{1-6}$ alkyl, $C_{1-6}$ haloalkyl, $C_{1-6}$ alkoxy, hydroxy, halo, amino, oxo, thio, or $C_{1-6}$ thioalkyl; and A is an amide of formula —C(O)—NH—$R^{11}$, wherein $R^{11}$ is selected from the group consisting of: $C_{1-8}$ alkyl, $C_{3-6}$ cycloalkyl, $C_6$ or $C_{10}$ aryl; $C_{7-16}$ aralkyl and $SO_2R^{11A}$ wherein $R^{11A}$ is $C_{1-8}$ alkyl, $C_{3-7}$ cycloalkyl or $C_{1-6}$ alkyl-$C_{3-7}$ cycloalkyl;

or A is a carboxylic acid or a pharmaceutically acceptable salt or ester thereof;

said process comprising the following steps:
(i) reacting a compound of formula II:

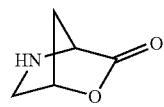
(II)

or a salt thereof, with a compound of formula III:

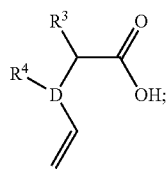
(III)

(ii) reacting the resulting compound of formula IV obtained in step (i):

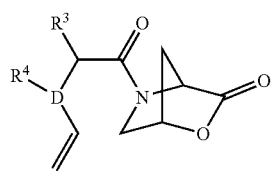
(IV)

with an aminocyclopropane compound of formula V

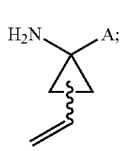
(V)

(iii) reacting the resulting compound of formula VI obtained in step (ii):

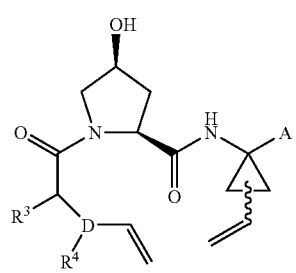
(VI)

with a compound of formula VII:

X—SO$_2$—R$^{12}$ (VII)

wherein X represents a suitable leaving group and R$^{12}$ is selected from p-tolyl, p-bromophenyl, p-nitrophenyl, methyl, trifluoromethyl, perfluorobutyl and 2,2,2-trifluoroethyl;

(iv) cyclyzing of the resulting diene compound of formula VIII obtained in step (iii):

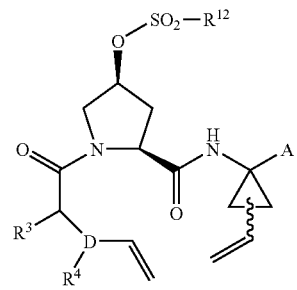
(VIII)

in the presence of a ruthenium catalyst; and
(v) reacting the resulting macrocyclic compound of formula IX obtained in step (iv):

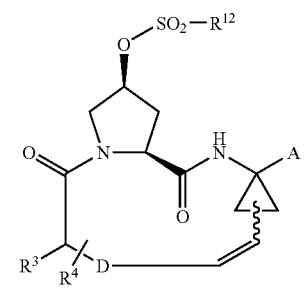
(IX)

with a compound of formula X:

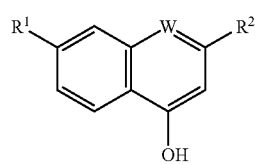
(X)

to obtain a compound of formula (I):

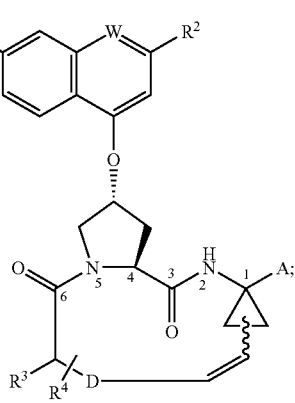
(I)

and when A is a carboxylic acid ester group in the resulting compound of formula (I), optionally subjecting the compound of formula (I) to reduction conditions to obtain a compound of formula (I) wherein A is a carboxylic acid group;

and when A is a carboxylic acid group in the resulting compound of formula (I), optionally coupling this compound with a sulfonamide of formula $R^{11A}SO_2NH_2$ in the presence of a suitable coupling agent, such as TBTU or HATU, to obtain a compound of formula (I) wherein A is —C(O)—NH—SO$_2$R$^{11A}$.

II. The Individual Steps of the Synthetic Method

Additional embodiments of the invention are directed to the individual steps of the multi-step general synthetic method described above and the individual intermediates used in these steps. These individual steps and intermediates of the present invention are described in detail below. All substituent groups are as defined above with respect to formula (I).

Step (i)

This step is directed to a process for preparing a compound of formula (IV):

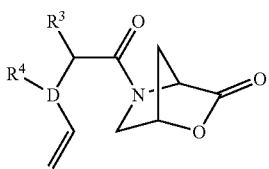

said process comprising:
reacting a compound of formula (II), or a salt thereof, with a compound of formula (III):

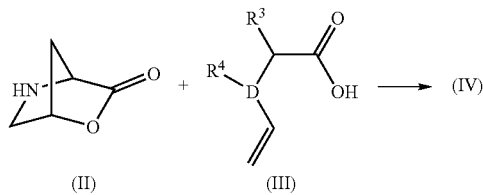

Peptide coupling between compounds of formula (II) and (III) could be obtained under a variety of suitable peptide coupling conditions known in the art, e.g., using conventional peptide coupling reagents such as DCC, EDC, TBTU, HBTU, HATU, DMTMM, HOBT, or HOAT in aprotic solvents such as dichloromethane, chloroform, DMF, NMP, DMSO.

In a specific embodiment, the compound of formula (II) is used in the form of its mesylate salt.

The cyclic lactone of formula (II), used as starting material can be obtained from a commercially available 4-hydroxyproline compound of formula (XI) using standard techniques as outlined in the following general scheme:

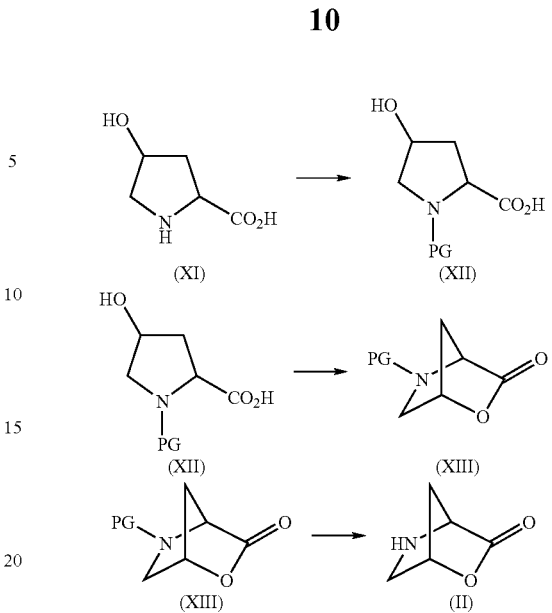

In the first step, an appropriate amino-protecting group is introduced onto the ring nitrogen atom of the 4-hydroxyproline compound of formula (XI) using conventional procedures. For example, compound of formula (XI) may be dissolved in a suitable solvent and reacted with an appropriate amino-protecting group introducing reagent. For example, and not intending to be limited in its scope, when Boc (tert-butyloxycarbonyl) is the desired protecting group, compound (XI) is reacted with the anhydride Boc$_2$O (or Boc-ON) in a solvent mixture such as Acetone/Water, MIBK/Water, THF/Water to which a base such as NaOH, KOH, LiOH, triethylamine, diisopropylethylamine, or N-methyl-pyrrolidine is added, the reaction being carried out at a temperature between 20–60° C.

In the second step, the protected 4-hydroxyproline compound of formula (XII) is converted to the cyclic lactone compound of formula (XIII) by reaction with an appropriate cyclizing reagent in a suitable solvent. In one embodiment, the OH functionality of the compound of formula (XII) is first reacted with an acid chloride (such as methanesulfonyl chloride, p-toluenesulfonyl choride, or trifluoromethanesulfonyl chloride) in a non-protic solvent (such as THF, dioxane, dichloromethane, chloroform, N-methylpyrrolidone, dimethyl sulfoxide, dimethylformamide, acetone, or methylisobutylketone) in the presence of a tertiary amine base (such as N-methyl-pyrrolidine, diisopropylethylamine or triethylamine) to render a compound with a suitable leaving group, followed by cyclization of the obtained compound in a polar non-protic solvent (such as dioxane) in the presence of a tertiary amine base to give the desired cyclic lactone of formula (XIII).

In the third step, the cyclic lactone compound of formula (XIII) is deprotected using conventional deprotection techniques, for example, by heating compound of formula (XIII) in a suitable solvent in the presence of an acid such as p-toluenesulfonic acid, HCl, HBr, HI, HF, H$_2$SO$_4$, H$_3$PO$_4$, methanesulfonic acid or trifluoroacetic acid, to obtain the compound of formula (II).

Compound of formula (II) may optionally be converted into a salt form by reaction with an appropriate acid. A specific example of the preparation of the mesylate salt of compound of formula (II) starting from an appropriate 4-hydroxyproline compound of formula (XI) is found in the Synthetic Examples section below.

The substituted acid compound of formula (III) used as a starting material may be obtained from commercially available materials using the techniques described in International Patent Application WO 00/59929.

Step (ii)

Step (ii) is directed to a process for preparing a compound of formula (VI):

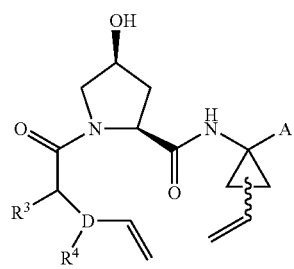

(VI)

said process comprising:

reacting a compound of formula (IV) with a compound of formula (V):

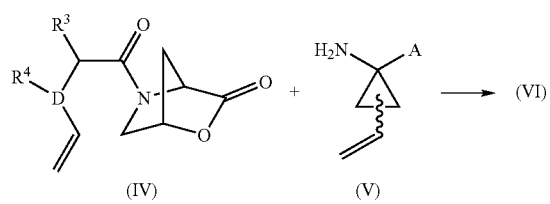

(IV)           (V)

A mixture of compound of formula (IV), compound of formula (V) and a suitable base, such as sodium 2-ethylhexanoate (SEH), in a suitable solvent (such as water, toluene, pyridine, a suitable solvent mixture such as toluene/THF or a suitable biphasic solvent system such as water/toluene) is stirred at a temperature from about 20° C. to about 80° C. until completion of the reaction. For work-up the organic layer may be washed and the product isolated after removing the solvent.

The compound of formula (V) used as starting material may be obtained from commercially available materials using the techniques described in International Patent Applications WO 00/59929, WO 00/09543, WO 00/09558 and U.S. Pat. No. 6,323,180 B1.

Step (iii)

Step (iii) is directed to a process for preparing a compound of formula (VIII):

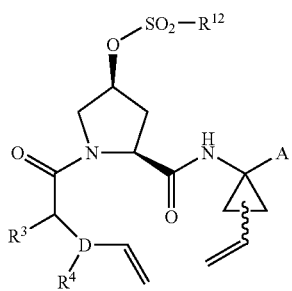

(VIII)

said process comprising:

reacting a compound of formula (VI) with a compound of formula (VII):

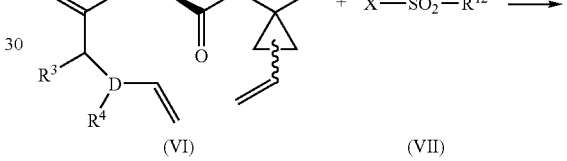

(VI)           (VII)

(VIII)

wherein X represents a suitable leaving group and $R^{12}$ is selected from p-tolyl, p-bromophenyl, p-nitrophenyl, methyl, trifluoromethyl, perfluorobutyl and 2,2,2-trifluoroethyl;

To a mixture of compound of formula (VI) and an organic base (such as DABCO, triethylamine, 1-methylpyrrolidine or pyridine) in an organic solvent (such as ether, dicholoromethane, cholorform or toluene), a solution of the compound of formula (VII) is added and the resultant mixture is stirred at ambient temperature (15–25° C.) until completion of reaction.

Step (iv)

Step (iv) is directed to a process for preparing a compound of formula (IX):

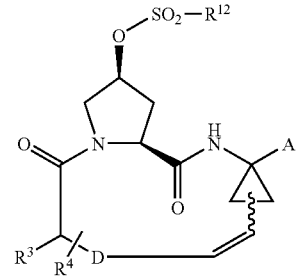

(IX)

said process comprising cyclyzing a diene compound of formula VIII in the presence of a suitable catalyst:

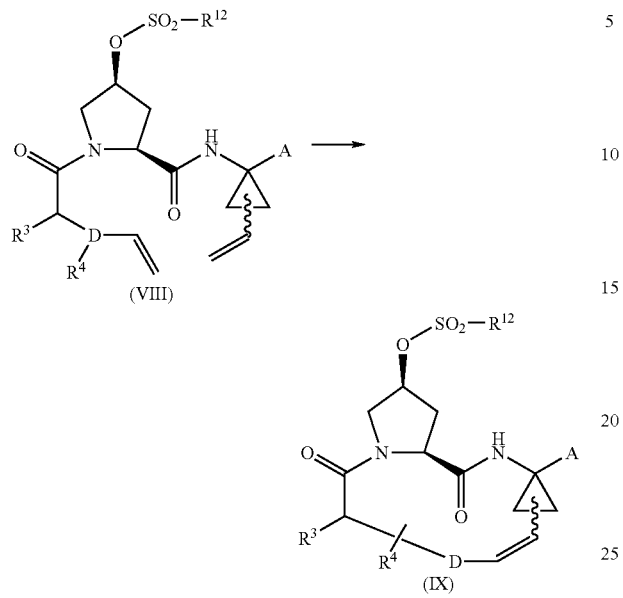

Suitable ring-closing catalysts for this step include, for example, ruthenium based catalysts used in olefin metathesis reactions, such as the catalysts described in WO 00/59929. Specific examples of suitable ruthenium-based catalysts include Grubb's catalyst (first and second generation), Hoveyda's catalyst (first and second generation) and Nolan's catalyst. In a specific embodiment, the catalyst used in this ring-closing step is a compound of formula (XIV):

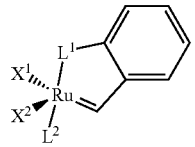

(XIV)

wherein
$X^1$ and $X^2$ each independently represent a covalently bonded ligand,
$L^1$ represents a ligand which is coordinatively bonded to the ruthenium atom and may be covalently bonded to the phenyl group, and
$L^2$ represents a ligand which is coordinatively bonded to the ruthenium atom.

In a particular embodiment of this step, the compound of formula (VIII) is dissolved in a degassed organic solvent (such as toluene or dichloromethane) to a concentration below about 0.02M, then treated with a ruthenium-based catalyst such as the compound of formula (XIV), at temperature from about 40° C. to about 110° C. until completion of reaction. Some or all of the ruthenium metal may be removed from the reaction mixture by treatment with a suitable heavy metal scavenger, such as THP or other agents known to scavenge heavy metals. The reaction mixture is washed with water, followed by partial concentration of the organic solution (e.g., by distillation process). The organic solution may be decolorized, such as by the addition of activated charcoal with subsequent filtration, and then is added to a suitable solvent at a suitable temperature, such as pre-cooled methylcyclohexane, which causes precipitation of the product compound of formula (IX) that is collected by filtration.

Step (v)
This step is directed to a process for preparing a compound of formula (I):

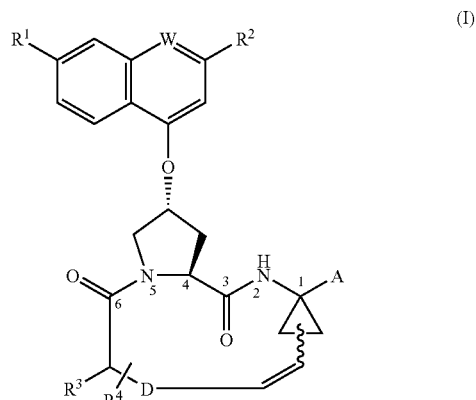

said process comprising reacting a macrocyclic compound of formula (IX) with a compound of formula (X):

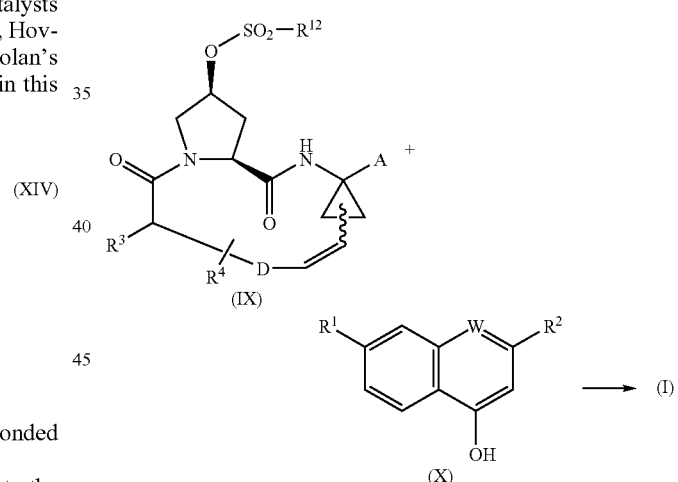

and when A is a carboxylic acid ester group in the resulting compound of formula (I), optionally subjecting the compound of formula (I) to hydrolysis conditions to obtain a compound of formula (I) wherein A is a carboxylic acid group;

and when A is a carboxylic acid group in the resulting compound of formula (I), optionally coupling this compound with a sulfonamide of formula $R^{114}SO_2NH_2$ in the presence of a suitable coupling agent, such as TBTU or HATU, to obtain a compound of formula (I) wherein A is $-C(O)-NH-SO_2R^{114}$.

Compounds of formula (IX) and (X) are mixed in a polar non-protic organic solvent (such as THF, Dioxane, dicholormethane, chloroform, N-methylpyrrolidone, dimethyl sulfoxide, dimethylformamide, acetone, or methylisobutylketone) in the presence of an inorganic or organic base (such as cesium carbonate, or DBU) at 40° C. to 100° C. until completion of reaction. Aqueous workup followed by crystallization from a suitable solvent such as ethylacetate-heptane or ethylacetate/methylcyclohexane provides the compounds of formula (I).

When A is a carboxylic acid ester group in formula (I), the esterified compound of formula (I) can optionally be subjected to hydrolysis conditions to obtain the corresponding free carboxylic acid compound. Hydrolysis can be carried out using conventional hydrolysis conditions known in the art. In a particular embodiment, for example, the esterified compound of formula (I) is dissolved in an organic solvent such as THF, and a suitable hydrolyzing agent such as lithium hydroxide monohydrate (LiOH.H$_2$O) is added followed by the addition of water. The resultant solution is stirred at a temperature from about 35° C. to about 50° C. At end of reaction, the solution is cooled, and the organic layer collected. A suitable solvent such as ethanol is added to the organic layer and the pH is adjusted to from about pH5 to about pH6. The mixture is then warmed to a temperature from about 40° C. to about 50° C. at which point water is added and solution is stirred whereupon the compound of formula (I) begins to precipitate. Upon completion of the precipitation, the solution is cooled to ambient temperature and the compound of formula (I) is collected by filtration, washed and dried.

Optionally, the compound of formula (I) can be further purified. In a particular embodiment of this purification step, the compound of formula (I) is dissolved in an aliphatic alcohol (e.g., ethanol), decolorized (e.g., treating the resulting solution with activated charcoal, followed by filtration) and then the solution is added to water at a temperature above about 55° C. Precipitation occurs during the addition of the solution to the water. The mixture is then cooled, and the crystalline product is collected, washed and dried.

The compound of formula (X) used as starting material may be obtained from commercially available materials using the techniques described in International Patent Applications WO 00/59929, WO 00/09543, WO 00/09558 and U.S. Pat. No. 6,323,180 B1.

III. Preferred Embodiments of The Compounds of Formula (I)

Preferred embodiments include compounds of formula (I) as described above, wherein the cyclopropyl moiety is selected from the 2 different diastereoisomers where the 1-carbon center of the cyclopropyl has the R configuration as represented by structures (i) and (ii):

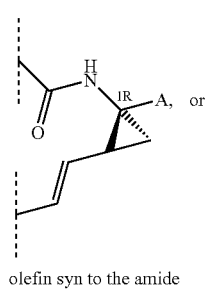

(i)

olefin syn to the amide

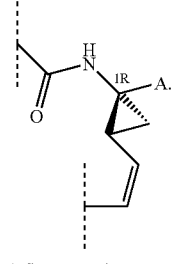

-continued (ii)

olefin syn to the A group

In a specific embodiment of the compounds of formula (I), the olefin group is in the configuration syn to the A group as represented by structure (ii) above;

W is N;

$R^1$ is H, $C_{1-6}$ alkyl, $C_{1-6}$ alkoxy, hydroxy, chloro, or $N(R^5)_2$, wherein $R^5$ is H or $C_{1-6}$ alkyl;

$R^2$ is H, $C_{1-6}$ thioalkyl, $C_{1-6}$ alkoxy, phenyl or Het selected from the following:

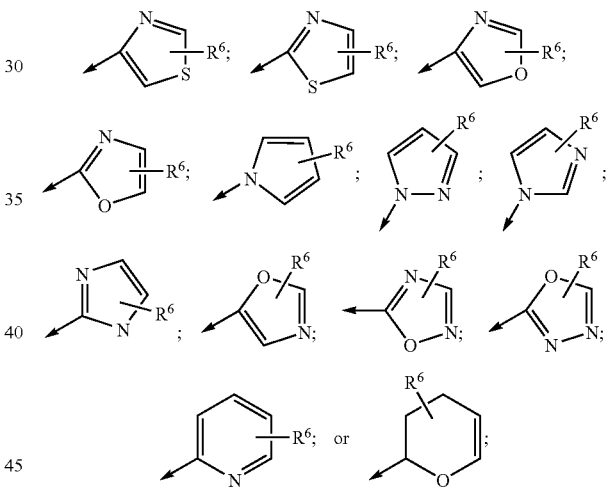

wherein $R^6$ is H, $C_{1-6}$ alkyl, NH—$R^7$, NH—C(O)—$R^7$, NH—C(O)—NH—$R^7$, wherein each $R^7$ is independently: H, $C_{1-6}$ alkyl, or $C_{3-6}$ cycloalkyl;

or $R^6$ is NH—C(O)—$OR^8$, wherein $R^8$ is $C_{1-6}$ alkyl;

$R^3$ is NH—C(O)—$OR^{10}$, wherein $R^{10}$ is $C_{1-6}$ alkyl, or $C_{3-6}$ cycloalkyl; and D is a 4 to 6-atom saturated alkylene chain;

$R^4$ is H or $C_{1-6}$ alkyl;

and A is a carboxylic acid or a pharmaceutically acceptable salt or ester thereof.

In another specific embodiment of the compounds of formula (I), the olefin group is in the configuration syn to the A group as represented by structure (ii) above;

W is N;

$R^1$ is $C_{1-3}$ alkoxy;

R² is

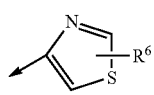

wherein R⁶ is NH—(C₁₋₄alkyl) or NH—(C₃₋₆cycloalkyl);
R³ is NH—C(O)—OR¹⁰, wherein R¹⁰ is butyl, cyclobutyl or cyclopentyl;
R⁴ is H or C₁₋₆ alkyl;
D is a 5-atom saturated alkylene chain; and
A is a carboxylic acid or a pharmaceutically acceptable salt or ester thereof.

The following table list compounds representative of the compounds of formula (I). A compound of the formula below:

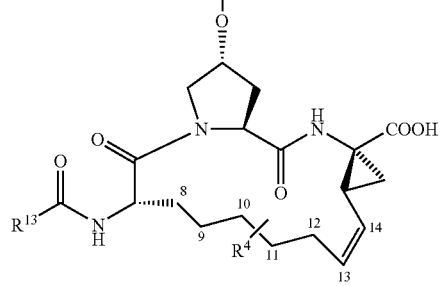

wherein the bond from position 14 to the cyclopropyl group is syn to the COOH, said 13,14 double bond is cis, R¹³, R⁴ and R² are defined as follows:

| Cpd # | R¹³: | R⁴: | R²: |
|---|---|---|---|
| 801 | cyclobutyl-O- | H | thiazole-NHAc; |
| 804 | (S)-tBuCH(CH₃)-NH- | H | thiazole-NHAc; |
| 805 | cyclopentyl-O- | H | pyrrolyl; |
| 807 | cyclopentyl-O- | H | OEt; |
| 808 | iPr-O- | H | OEt; |
| 809 | cyclopentyl-O- | H | thiazole-NHAc; |
| 810 | cyclopentyl-O- | H | thiazole-NHEt; |
| 811 | cyclopentyl-O- | H | thiazole-NHMe; |

-continued

| Cpd # | R13: | R4: | R2: |
|---|---|---|---|
| 812 | 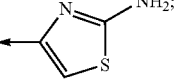 | H | 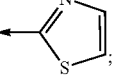 thiazol-2-ylamine; |
| 814 | 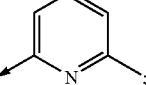 | H | thiazole; |
| 815 | cyclopentyloxy | H | pyridine; |
| 816 | 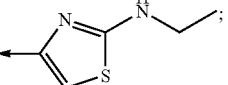 | H | 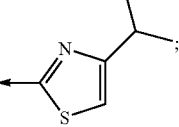 2-(ethylamino)thiazole; |
| 817 | cyclopentyloxy | H | 4-isopropylthiazole; |
| 818 | cyclopentyloxy | H | 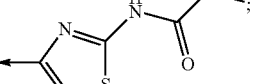 methyl thiazol-2-ylcarbamate; |
| 819 | cyclopentyloxy | H | 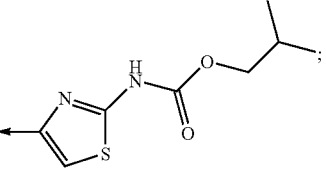 isobutyl thiazol-2-ylcarbamate; |
| 820 |  cyclobutyloxy | H | 2-(ethylamino)thiazole; |
| 821 | cyclopentyloxy | H | 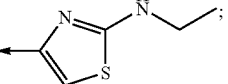 pyrazole; |
| 822 | cyclopentyloxy | H |  2-(isopropylamino)thiazole; |
| 823 | cyclopentyloxy | H | 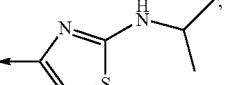 pyrazole; |
| 824 |  cyclopentyloxy | 10-(R)Me | OEt; |

-continued

| Cpd # | R$^{13}$: | R$^4$: | R$^2$: |
|---|---|---|---|
| 825 | 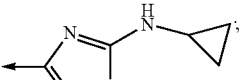 | H | 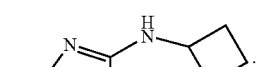 ; |
| 826 | 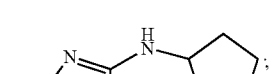 | H | 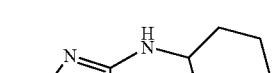 ; |
| 827 | 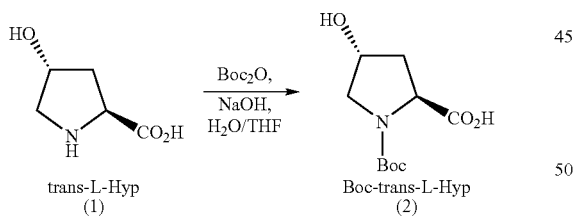 | H | 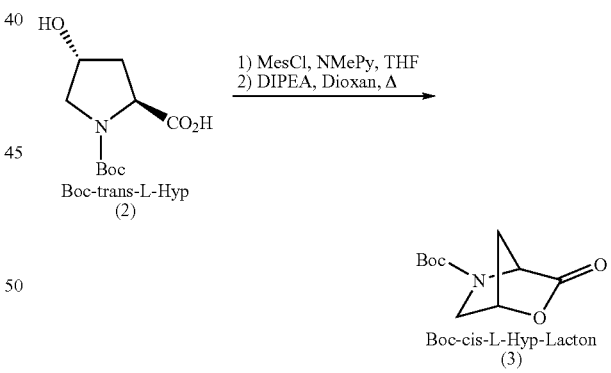 ; |
| and 828 | 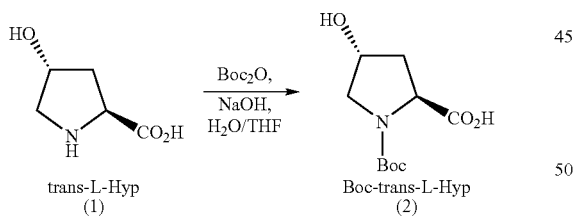 | H | 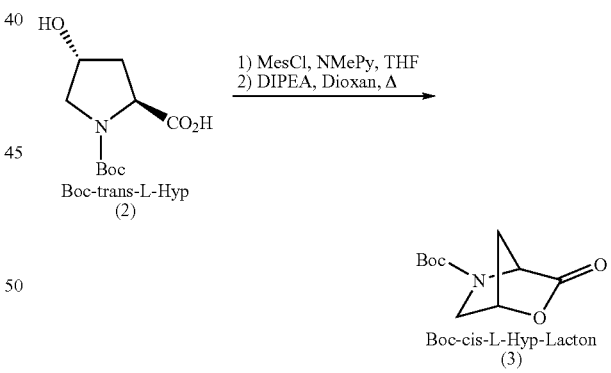 . |

A specific representative compound from the above table is Compound No. 822.

Additional specific compounds that are representative of the compounds of formula (I) may be found in WO 00/59929.

In order that this invention be more fully understood, the following examples of are set forth. These examples are for the purpose of illustrating embodiments of this invention, and are not to be construed as limiting the scope of the invention in any way.

SYNTHETIC EXAMPLES

Step 1: Introduction of the Boc-protecting Group; Synthesis of (2)

The amino-protection was done with the Boc-protecting-group. (1) (trans-4-hydroxy L-proline) (249.8 g, 1.905 mol) was dissolved in water (375 ml) and 45% sodium hydroxide solution (203 g, 2.286 mol). To ensure good phase transfer, tert-butanol (106 g) was added. In a different procedure, acetone was used instead of THF/tert-butanol. The reaction mixture was heated to 50° C. and the anhydride Boc$_2$O (424 g, 1.943 mol) was dissolved in THF (425 ml, or acetone) is slowly added. The reaction is exothermic and generates gas (CO$_2$) as the Boc$_2$O was added. If the reaction does not proceed as wanted, catalytic amounts of DMAP (2.3 g, 19 mmol) can be added. After the addition of the Boc$_2$O, the reaction mixture is kept ½–1 h at 50° C., and the THF was removed by partial distillation. The pH of the remaining solution was adjusted to about pH3 with concentrated HCl (204 g, 2.076 mol) and the product was then extracted with MIBK (1 liter) and again with MIBK (375 ml). The organic layer was heated and some of the solvent was distilled off to remove traces of water. The product was crystallized from this solution by adding MCH (1.25 l), isolated by filtration, washed twice with MCH (375 ml) and dried overnight at 40° C.

Yield: 77–78%, colorless crystals, F$_p$=126–128° C.

Step, 2: Formation of the Lactone; Synthesis of (3)

(2) (416.3 g, 1.8 mol) is dissolved in THF (2.08 l) and cooled with ice to a temperature from about −5— to about −10° C. Mesylchloride (392 g, 3.4 mol) and N-Methylpyrrolidine (429 g, 5 mol) is added and the mixture stirred for about 1½ h at about −5° C. The mixture is washed with water and heated up to reflux. Dioxane (2.08 l) is poured in and the THF is distilled off. After cooling down to room temperature, DIPEA (233 g, 1.8 mol) is added and the mixture is heated to reflux. After 1 h part of the solvent (830 ml) is distilled off, cooled to ambient temperature and a KHSO$_4$-solution (14.4 g in 2.08 l water) is poured in and the solution is allowed to cool down to room temperature. The resulting crystals are isolated by filtration, washed with water and dried overnight at 45° C.

Yield: 78–82%, colorless needles, $F_p$=111° C.

Step 3: Deprotection of the Lactone; Synthesis of (4)

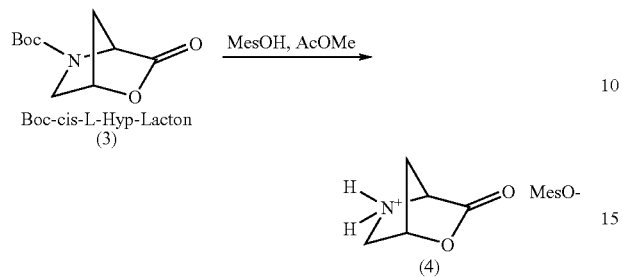

The lactone (3) (267 g, 1.25 mol) is dissolved in Methyl-isobutylketone (1467 ml). The suspension is heated up to 50° C. until the lactone is completely dissolved and a part of the solvent (130 ml) is distilled off to remove traces of water. Methansulfonic acid (240 g, 2.5 mol) is added slowly to the reaction mixture. During the addition gas is evolved ($CO_2$, Isobutene). The reaction mixture is allowed to cool to room temperature and the resulting crystals are isolated by filtration, washed twice with acetone (each 400 ml) and dried overnight at 40° C.

Yield: 93–98%, colorless crystals, 208–210° C.

Step 4: Coupling with (5): Synthesis of the Dipeptide (6)

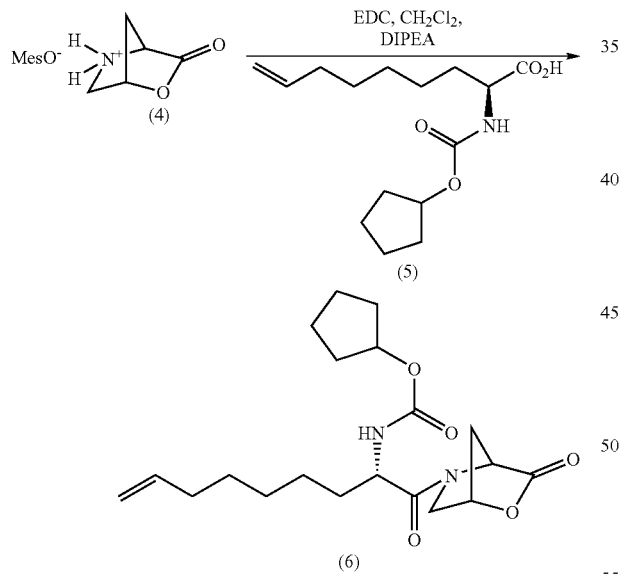

Compound (5) mayoptionally be obtained by releasing it from a salt form of the compound. For example, if a DCHA salt form is used (5)•DCHA (61.4 g, 132 mmol) is dissolved in toluene (160 ml) and the resulting solution is washed with diluted sulfuric acid (5.3 g in 80 ml water) and water (80 ml). After phase separation, the solution is treated with charcoal and filtered and the resulting solution stored at room temperature.

The deprotected lactone (4) (24.9 g, 119 mmol) and EDC.HCl (26.8 g, 140 mmol) are suspended in dichloromethane (140 ml) and cooled to room temperature. The suspension is treated with the (5)-solution generated before. To this suspension, di-isopropylethylamine (Hünigs-Base, 16.3 g, 130 mmol) is slowly added while the reaction is kept under nitrogen at temperatures below 20° C. The suspension is filtered, and the resulting solution is washed water (80 ml), diluted acetic acid (1.3 g in 80 ml water), 5% sodium bicarbonate solution (80 ml) and again with water (80 ml). After phase separation, dichloromethane is distilled off under reduced pressure. The resulting solution can directly be used for the next step. Otherwise, the product can be isolated by crystallization from MCH.

Yield: 95% (GC), yellowish solution, $F_p$=58–60° C.

Step 5: Synthesis of (8)

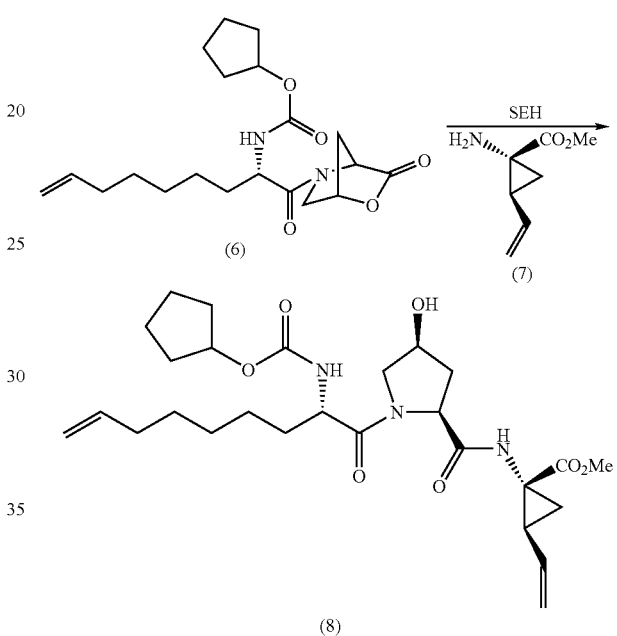

A mixture of (6) (10.0 g, 23.7 mmol, 1.0 eq.), (7) (7.6 g, 24.2 mmol, 1.02 eq.) and sodium 2-ethylhexanoate (SEH) (5.9 g, 35.6 mmol, 1.5 eq.) in water (43 ml) and toluene (12 ml) is stirred at 80° C. for 2 h. For work-up toluene (75 ml) is added at 80° C. After stirring and separation of the aqueous layer, the organic layer is washed with 1M $Na_2CO_3$ (3×30 ml), 0.5M HCl (30 ml) and water (2×30 ml). The solvent is removed under vacuum.

Yield of (8): 11.7 g, 22.5 mmol, 95%; purity: >95% (peak-area HPLC) as a slightly yellow oil.

Step 6. Brosylation of (8); Synthesis of (9)

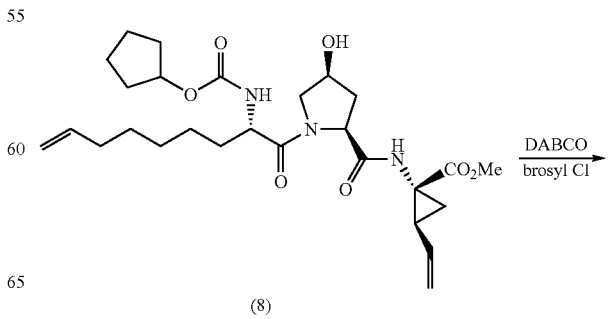

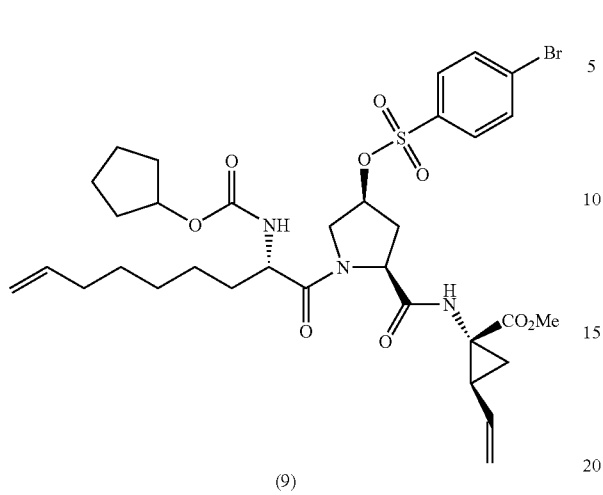

(9)

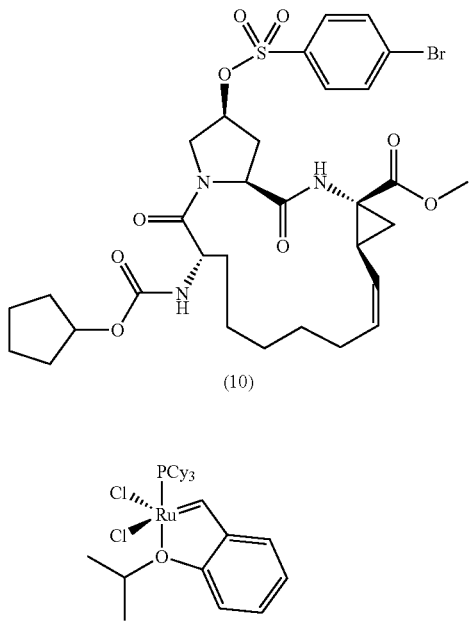

(10)

Hoveyda's Catalyst

To a mixture of (8) (10.7 g, 18.5 mmol, 1.0 eq.) and DABCO (3.3 g, 29.7 mmol, 1.6 eq.) and toluene (23 ml) a solution of 4-bromobenzenesulfonyl chloride (brosyl chloride, 6.6 g, 26.0 mmol, 1.4 eq.) in toluene (15 ml) is added slowly at room temperature. The mixture is stirred for 2 h. For work-up the organic layer is washed with 1M Na$_2$CO$_3$ (2×21 ml), diluted with THF (21 ml) and washed with 0.5M HCl (21 ml) and water (2×21 ml). The solvent is removed under vacuum.

Yield of (9): 12.3 g, 16.7 mmol, 90%; purity: >95% (peak-area HPLC) as a slightly orange oil. A charcoal treatment of the crude product is possible.

Step 7: Metathesis of (9) to (10)

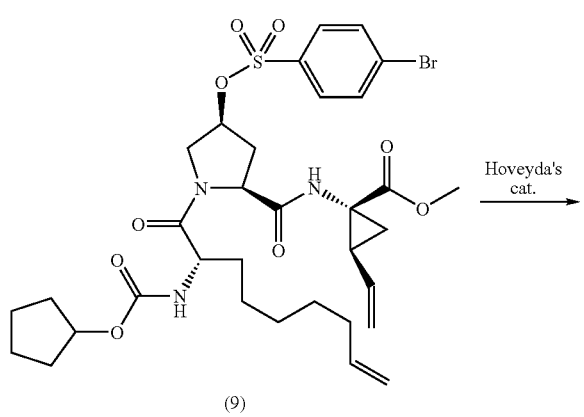

(9)

Preparation of the THP-solution (for an Experiment with 35.4 g (9)):

23.5 g Tetrakishydroxymethylphosphoniumchloride (80%, 98.7 mmol) is dissolved in isopropanol (35 ml) under a nitrogen atmosphere. Then 12.1 g (98.7 mmol) of a 45% KOH solution is added within 5 min while the solution is cooled (temperature 20–25° C.). After stirring the suspension for another 30 min under nitrogen, the mixture is filtered and the inorganic residue is washed with 20 ml of degassed isopropanol. The combined isopropanol solution is stored under a nitrogen atmosphere until use.

Metathesis Reaction:

In a reaction flask 3500 ml of toluene is degassed by bubbling nitrogen through the toluene. 35.2 g (47.7 mmol) of (9) are dissolved in 70 ml of degassed toluene and added into the reaction flask. The solution is heated up to 80° C. and 3 mol % of Hoveyda's catalyst is added under nitrogen in four portions over a period of 3 hours. After stirring for a further 60 min at the same temperature the conversion is checked by HPLC. In the case that the conversion is below 95%, additional Hoveyda's catalyst is added and the mixture is stirred until the conversion is >95% (during the reaction a slight stream of nitrogen is bubbled through the reaction mixture).

After cooling to 50° C. the THP solution is added to the reaction mixture. After stirring for 8.5 h at 50° C. the mixture is cooled to room temperature and extracted twice with 188 ml of degassed water, 188 ml of 0.5 M HCl, 188 ml of 0.5 M NaHCO$_3$ solution, and 188 ml of water.

Approximately 2800 ml of toluene are distilled off at 50° C. under partial pressure and the remaining solution is treated at 50° C. with 6.8 g of charcoal (Acticarbon L2S). The charcoal is then removed by filtration.

The remaining liquid filtrate (approx. 130 ml) is added over a period of 1 hour to 1.5 liters of precooled MCH (5° C.). After stirring for a further 30 min at 5° C. the precipitate is filtered and washed with 100 ml of MCH (several portions). The white solid is dried in vacuo at 25° C.

Yield (by weight): 38 g of an almost white powder

Step 8: Synthesis of (12):

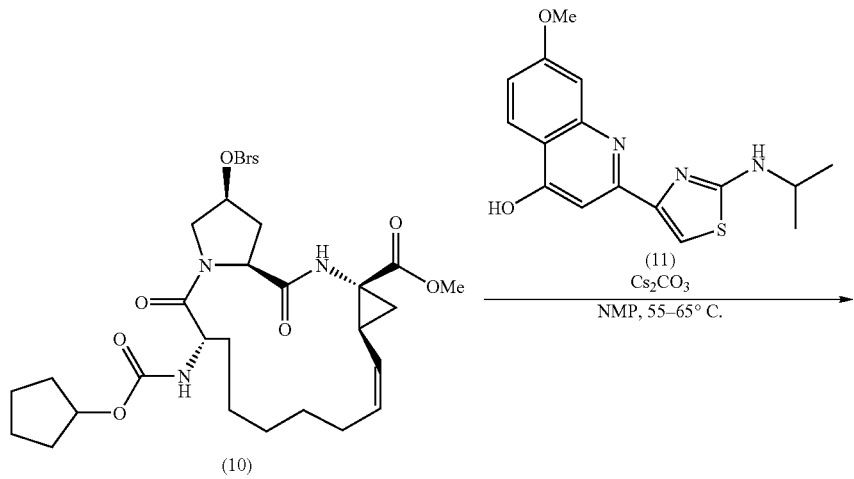

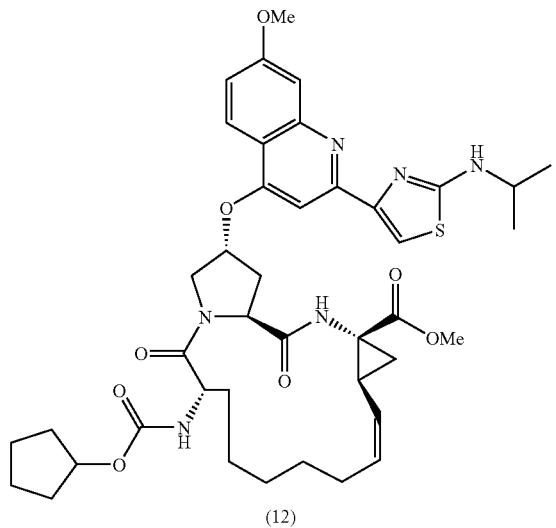

A mixture of (10) (1 eq.), $Cs_2CO_3$ (1 eq.), and (11) (1 eq.) in NMP is stirred for 8 h at 55 to 65° C. After completion of the reaction the mixture is diluted with ethylacetate and washed with 2.5% $NaHCO_3$ solution. The organic layer is extracted three times with a mixture of a 2.5% solution of $NaHCO_3$ and NMP. The organic layer is treated with charcoal, filtered, and the product is crystallised by the addition of n-heptane (or methylcyclohexane). The suspension is cooled to 5° C., the precipitate is filtered and washed with ethylacetate/n-heptane (or ethylacetate/methylcyclohexane) and dried in vacuo.

Yield: 60–70%, white crystals.

If necessary, the product can be recrystallised from ethylacetate/methylcyclohexane.

Step 9: Synthesis of Compound #822 crude:

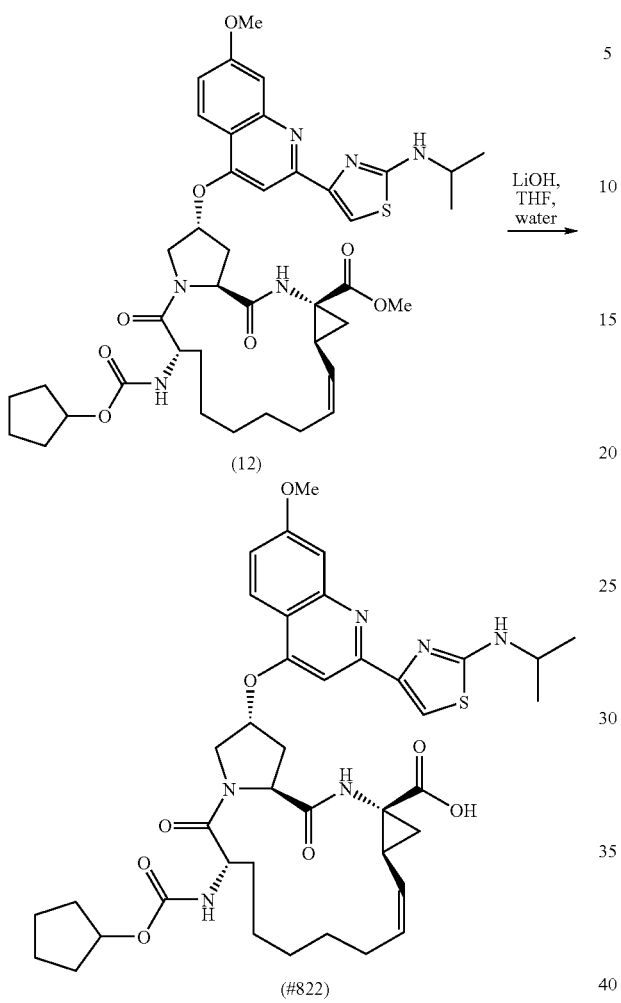

20 g (0.025 mol) of (12) is dissolved in 160 ml of THF and 2.45 g (0.0583 mmol) of LiOH.H$_2$O is added to the solution. After the addition of 54 ml of water the reaction mixture is stirred for at least 8 h at a temperature of 40–45° C. After complete conversion (HPLC) the biphasic system is cooled to 20–25° C. After separation of the layers (a small aqueous phase is separated) 54 ml of ethanol is added to the organic layer and the pH is adjusted to pH 5.5–5.7 by the addition of 1M HCl solution. The mixture is warmed to 40–45° C. and 80 ml of water are added over a period of at least 30 min (40–45° C.). During this procedure the solution becomes cloudy. The mixture is stirred for further 60 min at a temperature of 40–45° C. (after 15 min the product should precipitate). Further 80 ml of water are added at 40–45° C. over a period of at least 30 min and the mixture is stirred for another 60 min at the same temperature. The suspension is cooled to 20–25° C. and stirred at this temperature for 1 h. After filtration the precipitate is washed three times by 20 ml of water and dried in vacuo at 35° C. (slight stream of N$_2$).

yield: 17.7–18.7 g of (#822) crude (90–95%)

The product contains between 3 and 5% of water.

Step 10: Synthesis of Purified Compound #822:

10 g (0.0129 mol) (#822) crude are dissolved in 100 ml of ethanol at 20–25° C. Then the solution is treated with charcoal (5–20%), filtered and added to 240 ml of water at 70–75° C. over a period of 1 h. The mixture is cooled to 25–30° C. over a period of at least 1 h. After filtration the precipitate is washed with 40 ml of a 1.7/1 mixture of ethanol/water and dried in vacuo at 45° C. (slight stream of nitrogen).

yield: 9.2–9.7 g of (#822) pure (92–97%)

The product contains between 3 and 5% of water.

What is claimed is:

1. A process for preparing a compound of formula (I):

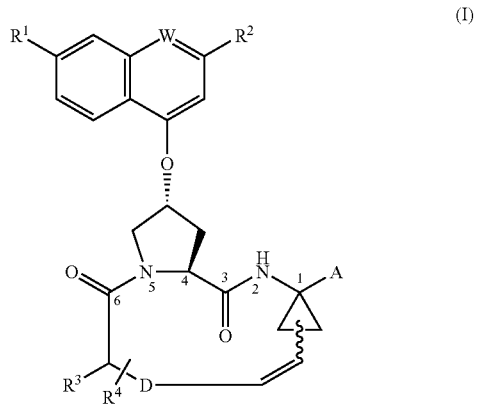

wherein W is CH or N,

R$_1$ is H, halo, C$_{1-6}$ alkyl, C$_{3-6}$ cycloalkyl, C$_{1-6}$ haloalkyl, C$_{1-6}$ alkoxy, C$_{3-6}$ cycloalkoxy, hydroxy, or N(R$^5$)$_2$, wherein each R$_5$ is independently H, C$_{1-6}$ alkyl or C$_{3-6}$ cycloalkyl;

R$^2$ is H, halo, C$_{1-6}$ alkyl, C$_{3-6}$ cycloalkyl, C$_{1-6}$ haloalkyl, C$_{1-6}$ thioalkyl, C$_{1-6}$ alkoxy, C$_{3-6}$ cycloalkoxy, C$_{2-7}$ alkoxy-C$_{1-6}$alkyl, C$_6$ or C$_{10}$ aryl or Het, wherein Het is a five-, six-, or seven-membered saturated or unsaturated heterocycle containing from one to four heteroatoms selected from nitrogen, oxygen and sulfur;

said cycloalkyl, aryl or Het being substituted with R$^6$, wherein R$^6$ is H, halo, C$_{1-6}$ alkyl, C$_{3-6}$ cycloalkyl, C$_{1-6}$ alkoxy, C$_{3-6}$ cycloalkoxy, NO$_2$, N(R$^7$)$_2$, NH—C(O)—R$^7$; or NH—C(O)—NH—R$^7$, wherein each R$^7$ is independently: H, C$_{1-6}$ alkyl or C$_{3-6}$ cycloalkyl;

or R$^6$ is NH—C(O)—OR$^8$ wherein R$^8$ is C$_{1-6}$ alkyl or C$_{3-6}$ cycloalkyl;

R$^3$ is hydroxy, NH$_2$, or a group of formula —NH—R$^9$, wherein R$^9$ is C$_6$ or C$_{10}$ aryl, heteroaryl, —C(O)—R$^{10}$, C(O)—NHR$^{10}$ or —C(O)—OR$^{10}$, wherein R$^{10}$ is C$_{1-6}$ alkyl or C$_{3-6}$ cycloalkyl;

D is a 3 to 7-atom saturated alkylene chain;

R$^4$ is H, or from one to three substituents on said chain D with up to two of these substitutents possible on any single carbon atom of said chain D, said substituent independently selected from the group consisting of: C$_{1-6}$ alkyl, C$_{1-6}$ haloalkyl, C$_{1-6}$ alkoxy, hydroxy, halo, amino, oxo, thio, or C$_{1-6}$ thioalkyl; and A is an amide of formula —C(O)—NH—R$^{11}$, wherein R$^{11}$ is selected from the group consisting of: C$_{1-8}$ alkyl, C$_{3-6}$ cycloalkyl, C$_6$ or C$_{10}$ aryl; C$_{7-16}$ aralkyl and SO$_2$R$^{11A}$ wherein R$^{11A}$ is C$_{1-8}$ alkyl, C$_{3-7}$ cycloalkyl or C$_{1-6}$ alkyl-C$_{3-7}$ cycloalkyl;

or A is a carboxylic acid or a pharmaceutically acceptable salt or ester thereof;

said process comprising reacting a macrocyclic compound of formula (IX) with a compound of formula (X) in a polar non-protic organic solvent in the presence of an organic or inorganic base:

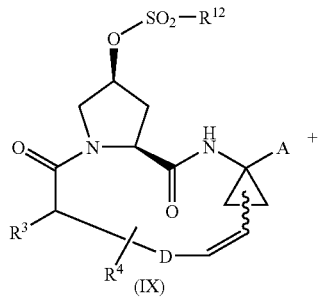

(IX)

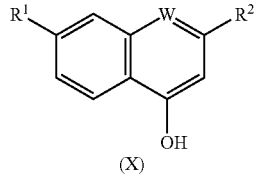

(X)

wherein W, $R^1$, $R^2$, $R^3$, $R^4$, D and A are as defined for formula (I), and $R^{12}$ is selected from p-tolyl, p-bromophenyl, p-nitrophenyl, methyl, trifluoromethyl, perfluorobutyl and 2,2,2-trifluoroethyl;

and when A is a carboxylic acid ester group in the resulting compound of formula (I), optionally subjecting the compound of formula (I) to hydrolysis conditions to obtain a compound of formula (I) wherein A is a carboxylic acid group;

and when A is a carboxylic acid group in the resulting compound of formula (I), optionally coupling this compound with a sulfonamide of formula $R^{11A}SO_2NH_2$ in the presence of a suitable coupling agent to obtain a compound of formula (I) wherein A is —C(O)—NH—$SO_2R^{11A}$.

2. A process according to claim 1, wherein in the compound of formula (I): the olefin group is in the configuration syn to the A group as represented by structure below:

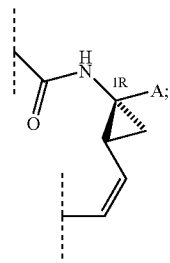

W is N;
$R^1$ is H, $C_{1-6}$ alkyl, $C_{1-6}$ alkoxy, hydroxy, chloro, or $N(R^5)_2$, wherein $R^5$ is H or $C_{1-6}$ alkyl;

$R^2$ is H, $C_{1-6}$ thioalkyl, $C_{1-6}$ alkoxy, phenyl or Het selected from the following:

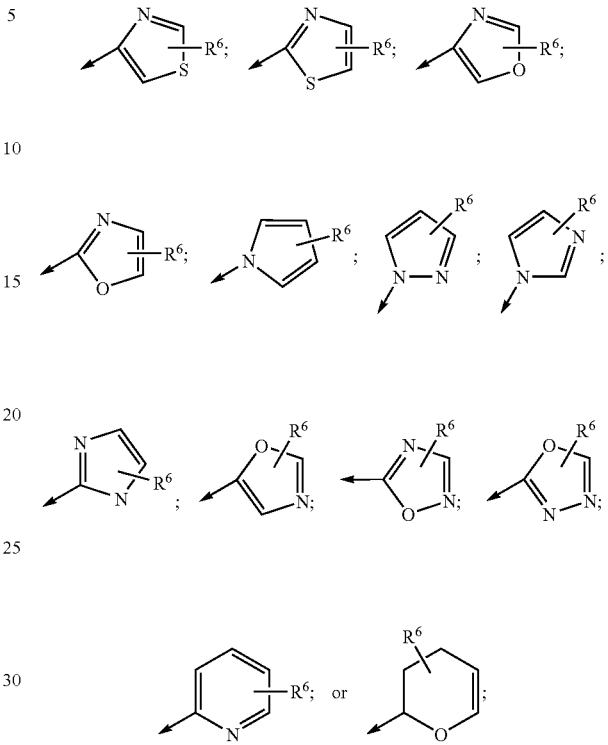

wherein $R^6$ is H, $C_{1-6}$ alkyl, NH—$R^7$, NH—C(O)—$R^7$, NH—C(O)—NH—$R^7$,
wherein each $R^7$ is independently: H, $C_{1-6}$ alkyl, or $C_{3-6}$ cycloalkyl;
or $R^6$ is NH—C(O)—$OR^8$, wherein $R^8$ is $C_{1-6}$ alkyl;
$R^3$ is NH—C(O)—$OR^{10}$, wherein $R^{10}$ is $C_{1-6}$ alkyl, or $C_{3-6}$ cycloalkyl; and
D is a 4 to 6-atom saturated alkylene chain;
$R^4$ is H or $C_{1-6}$ alkyl;
and A is a carboxylic acid or a pharmaceutically acceptable salt or ester thereof.

3. A process according to claim 1, wherein in the compound of formula (I): the olefin group is in the configuration syn to the A group as represented by structure below:

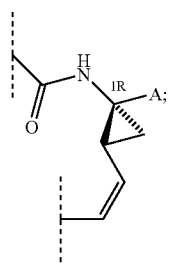

W is N;
$R^1$ is $C^{1-3}$ alkoxy;

$R^2$ is

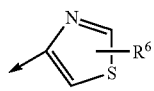

wherein $R^6$ is NH—($C_{1-4}$alkyl) or NH—($C_{3-6}$cycloalkyl);

$R^3$ is NH—C(O)—$OR^{10}$, wherein $R^{10}$ is butyl, cyclobutyl or cyclopentyl;

$R^4$ is H or $C_{1-6}$ alkyl;

D is a 5-atom saturated alkylene chain; and

A is a carboxylic acid or a pharmaceutically acceptable salt or ester thereof.

4. A process according to claim 1, wherein the compound of formula (I) is selected from the compounds in the following table:

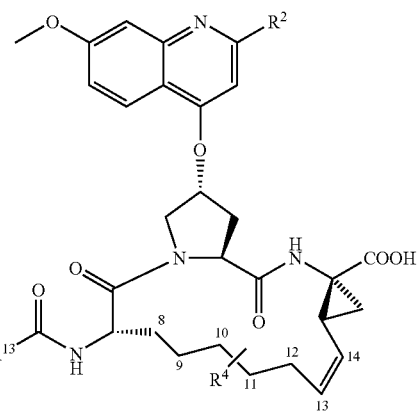

wherein the bond from position 14 to the cyclopropyl group is syn to the COOH, said 13,14 double bond is cis, $R^{13}$, $R^4$ and $R^2$ are defined as follows:

| Cpd # | $R^{13}$: | $R^4$: | $R^2$: |
|---|---|---|---|
| 801 | cyclobutyl-O— | H | thiazol-NHC(O)CH₃ |
| 804 | t-Bu-CH(CH₃)-NH— | H | thiazol-NHC(O)CH₃ |
| 805 | cyclopentyl-O— | H | pyrrolyl |
| 807 | cyclopentyl-O— | H | OEt; |
| 808 | iPr-O— | H | OEt; |
| 809 | cyclopentyl-O— | H | thiazol-NHC(O)CH₃ |
| 810 | cyclopentyl-O— | H | thiazol-NHEt; |
| 811 | cyclopentyl-O— | H | thiazol-NHMe; |

-continued
| Cpd # | R¹³: | R⁴: | R²: |
|---|---|---|---|
| 812 | 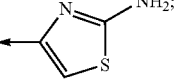 | H | 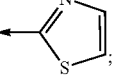 thiazol-2-amine; |
| 814 | 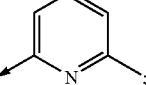 | H | thiazole; |
| 815 | 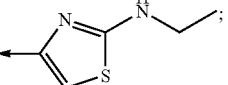 | H | pyridine; |
| 816 | 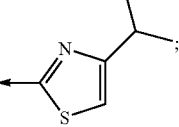 | H | 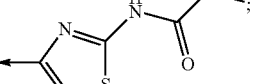 2-(ethylamino)thiazole; |
| 817 | 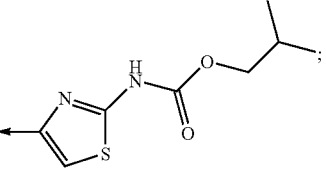 | H | 4-isopropylthiazole; |
| 818 |  | H | methyl thiazol-2-ylcarbamate; |
| 819 | 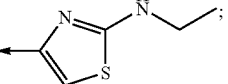 | H | isobutyl thiazol-2-ylcarbamate; |
| 820 |  | H | 2-(ethylamino)thiazole; |
| 821 | | H | pyrazole; |
| 822 | | H | 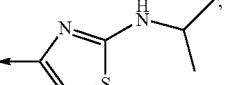 2-(isopropylamino)thiazole; |
| 823 | | H | pyrazole; |
| 824 | 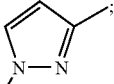 | 10-(R)Me | OEt; |

| Cpd # | R¹³ | R⁴ | R² |
|---|---|---|---|
| 825 | 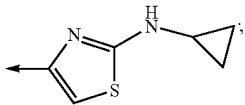 | H | 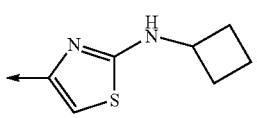 ; |
| 826 | 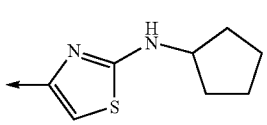 | H | 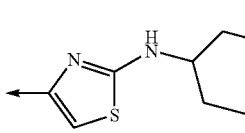 ; |
| 827 | 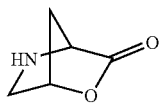 | H | 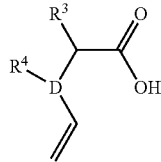 ; |
| and 828 | 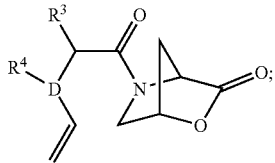 | H | 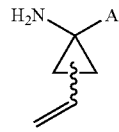 . |

5. A process according to claim 4, wherein the compound of formula (I) is Compound No. 822.

6. A process according to claim 1, wherein the compound of formula (IX) is prepared by a process comprising:

(i) reacting a compound of formula II:

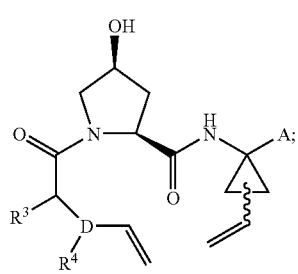

(II)

or a salt thereof, with a compound of formula III:

(III)

under suitable peptide coupling conditions to obtain a compound of formula IV:

(IV)

(ii) reacting the resulting compound of formula IV obtained in step (i) with an aminocyclopropane compound of formula V:

(V)

in the presence of a suitable base in suitable solvent to obtain a compound of formula VI:

(VI)

(iii) reacting the resulting compound of formula VI obtained in step (ii) with a compound of formula VII:

$$X-SO_2-R^{12}$$ (VII)

wherein X represents a suitable leaving group and $R^{12}$ is selected from p-tolyl, p-bromophenyl, p-nitrophenyl, methyl, trifluoromethyl, perfluorobutyl and 2,2,2-trifluoro ethyl, in the presence of an organic base in an organic solvent to obtain a compound of formula VIII:

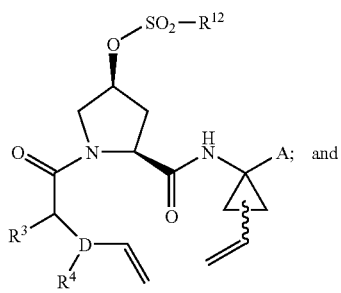
(VIII)

(iv) cyclyzing the resulting compound of formula VIII obtained in step (iii) in the presence of a suitable catalyst to obtain a compound of formula IX:

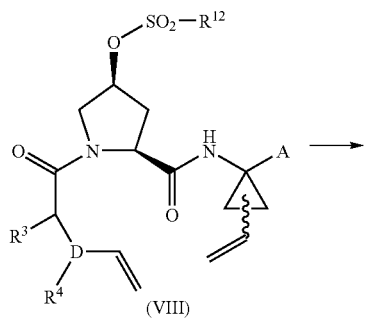
(VIII)

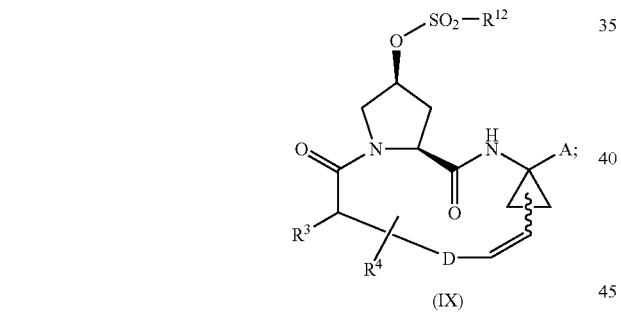
(IX)

wherein $R^3$, $R^4$, D and A are as defined in claim 1.

7. A compound of the formula (IV):

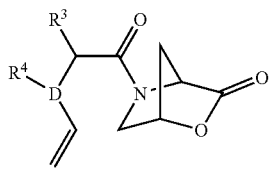
(IV)

wherein $R^3$ is hydroxy, $NH_2$, or a group of formula —NH—$R^9$, wherein $R^9$ is $C_6$ or $C_{10}$ aryl, heteroaryl, —C(O)—$R^{10}$, C(O)—NH$R^{10}$ or —C(O)—O$R^{10}$, wherein $R^{10}$ is $C_{1-6}$ alkyl or $C_{3-6}$ cycloalkyl;

D is a 3 to 7-atom saturated alkylene chain;

$R^4$ is H, or from one to three substituents on said chain D with up to two of these substituents possible on any single carbon atom of said chain D, said substituent independently selected from the group consisting of: $C_{1-6}$ alkyl, $C_{1-6}$ haloalkyl, $C_{1-6}$ alkoxy, hydroxy, halo, amino, oxo, thio, or $C_{1-6}$ thioalkyl.

8. A process for preparing a compound of formula (IV) according to claim 7, said process comprising reacting a compound of formula (II) with a compound of formula (III) under suitable peptide coupling conditions to obtain a compound of formula (IV):

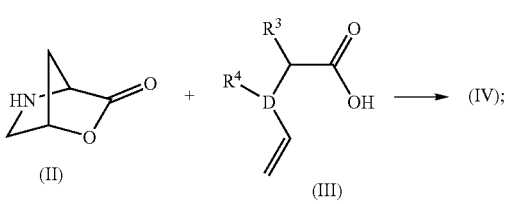

wherein $R^3$, $R^4$ and D are as defined in claim 7.

9. A process for preparing a compound of the following formula (VI):

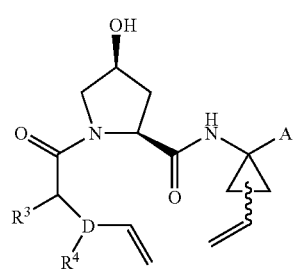
(VI)

wherein:

$R^3$ is hydroxy, $NH_2$, or a group of formula —NH—$R^9$, wherein $R^9$ is $C_6$ or $C_{10}$ aryl, heteroaryl, —C(O)—$R^{10}$, —C(O)—NH$R^{10}$ or —C(O)—O—$C_{3-6}$ cycloalkyl, wherein $R^{10}$ is $C_{1-6}$ alkyl or $C_{3-6}$ cycloalkyl;

D is a 3 to 7-atom saturated alkylene chain;

$R^4$ is H, or from one to three substituents on said chain D with up to two of these substituents possible on any single carbon atom of said chain D, said substituent independently selected from the group consisting of: $C_{1-6}$ alkyl, $C_{1-6}$ haloalkyl, $C_{1-6}$ alkoxy, hydroxy, halo, amino, oxo, thio, or $C_{1-6}$ thioalkyl; and A is an amide of formula —C(O)—NH—$R^{11}$, wherein $R^{11}$ is selected from the group consisting of: $C_{1-8}$ alkyl, $C_{3-6}$ cycloalkyl, $C_6$ or $C_{10}$ aryl; $C_{7-16}$ aralkyl and $SO_2R^{11A}$ wherein $R^{11A}$ is $C_{1-8}$ alkyl, $C_{3-7}$ cycloalkyl or $C_{1-6}$ alkyl-$C_{3-7}$ cycloalky;

or A is a carboxylic acid or a pharmaceutically acceptable salt or ester thereof, said process comprising reacting a compound of formula (IV) with a compound of formula (V) in the presence of a suitable base in suitable solvent to obtain a compound of formula (VI):

(IV) + (V) → (VI);

wherein R³, R⁴, D and A are as defined in formula (VI) above.

10. A compound of the formula (VIII):

(VIII)

wherein:
- R³ is hydroxy, NH₂, or a group of formula —NH—R⁹, wherein R⁹ is $C_6$ or $C_{10}$ aryl, heteroaryl, —C(O)—R¹⁰, —C(O)—NHR¹⁰ or —C(O)—OR¹⁰, wherein R¹⁰ is $C_{1-6}$ alkyl or $C_{3-6}$ cycloalkyl;
- D is a 3 to 7-atom saturated alkylene chain;
- R⁴ is H, or from one to three substituents on said chain D with up to two of these substituents possible on any single carbon atom of said chain D, said substituent independently selected from the group consisting of: $C_{1-6}$ alkyl, $C_{1-6}$ haloalkyl, $C_{1-6}$ alkoxy, hydroxy, halo, amino, oxo, thio, or $C_{1-6}$ thioalkyl; and
- A is an amide of formula —C(O)—NH—R¹¹, wherein R¹¹ is selected from the group consisting of: $C_{1-8}$ alkyl, $C_{3-6}$ cycloalkyl, $C_6$ or $C_{10}$ aryl; $C_{7-16}$ aralkyl and SO₂R¹¹ᴬ wherein R¹¹ᴬ is $C_{1-8}$ alkyl, $C_{3-7}$ cycloalkyl or $C_{1-6}$ alkyl-$C_{3-7}$ cycloalkyl;
- or A is a carboxylic acid or a pharmaceutically acceptable salt or ester thereof; and
- R¹² is selected from p-tolyl, p-bromophenyl, p-nitrophenyl, methyl, trifluoromethyl, perfluorobutyl and 2,2,2-trifluoroethyl.

11. A compound of formula (VIII) according to claim 10, wherein:
the olefin group is in the configuration syn to the A group as represented by structure below:

- R³ is NH—C(O)—OR¹⁰, wherein R¹⁰ is $C_{1-6}$ alkyl, or $C_{3-6}$ cycloalkyl; and
- D is a 4 to 6-atom saturated alkylene chain;
- R⁴ is H or $C_{1-6}$ alkyl;
- A is a carboxylic acid or a pharmaceutically acceptable salt or ester thereof; and
- R¹² is selected from p-tolyl, p-bromophenyl and p-nitrophenyl.

12. A compound of formula (VIII) according to claim 10, wherein:
the olefin group is in the configuration syn to the A group as represented by structure below:

- R³ is NH—C(O)—OR¹⁰, wherein R¹⁰ is butyl, cyclobutyl or cyclopentyl;
- R⁴ is H or $C_{1-6}$ alkyl;
- D is a 5-atom saturated alkylene chain;
- A is a carboxylic acid or a pharmaceutically acceptable salt or ester thereof; and
- R¹² is p-bromophenyl.

13. A process for preparing a compound of formula (VIII) according to claim 10, said process comprising reacting a compound of formula (VI) with a compound of formula (VII), wherein R³, R⁴, D, A and R¹² are as defined in claim 10 and X represents a suitable leaving group, in the presence of an organic base in an organic solvent to obtain a compound of formula VIII:

(VI) + X—SO₂—R¹² (VII) → (VIII).

14. A compound of formula (IX):

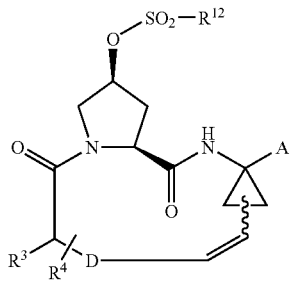

(IX)

wherein $R^3$ is hydroxy, $NH_2$, or a group of formula —NH—$R^9$, wherein $R^9$ is $C_6$ or $C_{10}$ aryl, heteroaryl, —C(O)—$R^{10}$, —C(O)—NH$R^{10}$ or —C(O)—O$R^{10}$, wherein $R^{10}$ is $C_{1-6}$ alkyl or $C_{3-6}$ cycloalkyl;

D is a 3 to 7-atom saturated alkylene chain;

$R^4$ is H, or from one to three substituents on said chain D with up to two of these substituents possible on any single carbon atom of said chain D, said substituent independently selected from the group consisting of: $C_{1-6}$ alkyl, $C_{1-6}$ haloalkyl, $C_{1-6}$ alkoxy, hydroxy, halo, amino, oxo, thio, or $C_{1-6}$ thioalkyl; and A is an amide of formula —C(O)—NH—$R^{11}$, wherein $R^{11}$ is selected from the group consisting of: $C_{1-8}$ alkyl, $C_{3-6}$ cycloalkyl, $C_6$ or $C_{10}$ aryl; $C_{7-16}$ aralkyl and $SO_2R^{11A}$ wherein $R^{11A}$ is $C_{1-8}$ alkyl, $C_{3-7}$ cycloalkyl or $C_{1-6}$ alkyl-$C_{3-7}$ cycloalkyl;

or A is a carboxylic acid or a pharmaceutically acceptable salt or ester thereof; and $R^{12}$ is selected from p-tolyl, p-bromophenyl, p-nitrophenyl, methyl, trifluoromethyl, perfluorobutyl and 2,2,2-trifluoroethyl.

15. A compound of formula (IX) according to claim 14, wherein:

the olefin group is in the configuration syn to the A group as represented by structure below:

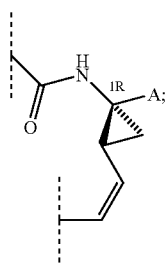

$R^3$ is NH—C(O)—O$R^{10}$, wherein $R^{10}$ is $C_{1-6}$ alkyl, or $C_{3-6}$ cycloalkyl; and D is a 4 to 6-atom saturated alkylene chain;

$R^4$ is H or $C_{1-6}$ alkyl;

A is a carboxylic acid or a pharmaceutically acceptable salt or ester thereof; and $R^{12}$ is selected from p-tolyl, p-bromophenyl and p-nitrophenyl.

16. A compound of formula (IX) according to claim 14, wherein:

the olefin group is in the configuration syn to the A group as represented by structure below:

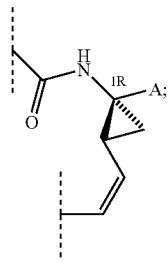

$R^3$ is NH—C(O)—O$R^{10}$, wherein $R^{10}$ is butyl, cyclobutyl or cyclopentyl;

$R^4$ is H or $C_{1-6}$ alkyl;

D is a 5-atom saturated alkylene chain;

A is a carboxylic acid or a pharmaceutically acceptable salt or ester thereof; and $R^{12}$ is p-bromophenyl.

17. A process for preparing a compound of formula (IX) according to claim 14, said process comprising cyclyzing the diene compound of formula (VIII) in the presence of a suitable catalyst to obtain a compound of formula (IX):

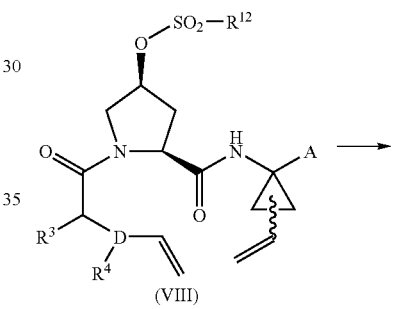

(VIII)

(IX)

wherein $R^3$, $R^4$, D, A and $R^{12}$ are as defined in claim 14.

18. A process according to claim 17, wherein the catalyst is a ruthenium-based catalyst.

19. A process according to claim 18, wherein the ruthenium-based catalyst is a compound of formula (XIV):

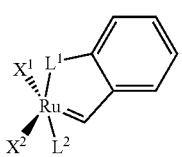

(XIV)

wherein
X¹ and X² each independently represent a covalently bonded ligand,

L¹ represents a ligand which is coordinatively bonded to the ruthenium atom and may be covalently bonded to the phenyl group, and L² represents a ligand which is coordinatively bonded to the ruthenium atom.

20. A process according to claim 17, wherein the compound of formula (VIII) is dissolved in a degassed organic solvent to a concentration below about 0.02M, then treated with a ruthenium-based catalyst at a temperature from about 40° C. to about 110° C.

21. A process according to claim 20, wherein the organic solvent is toluene or dichloromethane.

22. A process according to claim 20, wherein the ruthenium-based catalyst is a compound of formula (XIV):

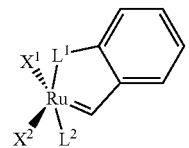

(XIV)

wherein
X¹ and X² each independently represent a covalently bonded ligand,
L¹ represents a ligand which is coordinatively bonded to the ruthenium atom and may be covalently bonded to the phenyl group, and
L² represents a ligand which is coordinatively bonded to the ruthenium atom.
n

* * * * *